United States Patent [19]

Ratty et al.

[11] Patent Number: 5,723,719
[45] Date of Patent: Mar. 3, 1998

[54] TRANSGENIC MOUSE AS MODEL FOR DISEASES INVOLVING DOPAMINERGIC DYSFUNCTION

[75] Inventors: Anil K. Ratty, Kent Ridge Crescent, Singapore; Stanley D. Glick, Williamstown, Mass.; John J. Mullins, Edinburgh, United Kingdom; Lawrence W. Fitzgerald, Milford, Conn.; Kenneth W. Gross, East Concord, N.Y.

[73] Assignee: Health Research Inc., Buffalo, N.Y.

[21] Appl. No.: 389,191

[22] Filed: Feb. 15, 1995

Related U.S. Application Data

[63] Continuation-in-part of Ser. No. 36,988, Mar. 25, 1993, abandoned, which is a continuation-in-part of Ser. No. 742,601, Aug. 8, 1991, abandoned.

[51] Int. Cl.$^6$ .............................. C12N 5/00; C12N 15/00; A61K 49/00
[52] U.S. Cl. ........................... 800/2; 800/DIG. 2; 424/9.2
[58] Field of Search ................................... 800/2, DIG. 1; 424/9.2

*Primary Examiner*—Deborah Crouch
*Attorney, Agent, or Firm*—Hodgson, Russ, Andrews, Woods & Goodyear

[57] ABSTRACT

The present invention provides a transgenic mouse which exhibits a circling phenotype as a result of insertional mutagenesis. The insertional mutant was caused by introducing genetic material into the genome of the mouse, or an ancestor thereof, at an embryonic stage. The genetic material appears to alter or disrupt an endogenous genetic locus affecting motor function, resulting in the mutation. More particularly, transgenic mouse lines were made by microinjection of about 24 kb XhoI genomic DNA fragment containing the mouse Ren-$2^d$ renin gene into BCF$_1$, fertilized eggs. One transgenic mouse line, designated TgX15 (also known as chakragati mice), bred to homozygosity was found to exhibit a circling phenotype. The transgenic mouse line TgX15 may be an important resource for investigating the molecular genetic mechanisms that determine specific aspects of brain function and behavior. Also, these mice may be useful to evaluate new and potentially more effective agents for the therapeutic treatment of disorders involving dopaminergic dysfunction such as Parkinsonism and schizophrenia.

6 Claims, 2 Drawing Sheets

TRANSGENIC MOUSE AS MODEL FOR DISEASES INVOLVING DOPAMINERGIC DYSFUNCTION

This application is a continuation-in-part of U.S. Ser. No. 08/036,988 filed Mar. 25, 1993, now abandoned, which was a continuation in part of U.S. Ser. No. 742,601 filed Aug. 8, 1991, which former applications are herein incorporated by reference and now abandoned.

This invention was made with government support under grant numbers HL35792-04 and GM30248-07 awarded by the national Institutes of Health. The government has certain rights in the invention.

FIELD OF THE INVENTION

This invention relates generally to transgenic animals and more particularly, to a transgenic mouse expressing a circling behavior phenotype as a result of an insertional mutation, wherein transgene integration apparently disrupted an endogenous genetic locus affecting motor function.

BACKGROUND OF THE INVENTION

Transgenic mice technology involves the introduction of new or altered genetic material into the mouse germ line by microinjection, retroviral infection or embryonic stem cell transfer. This results in lineages that carry the new integrated genetic material. Insertional mutagenesis occurs when integration of the microinjected genetic material into the host genome alters an endogenous gene resulting in a mutation. Methods of transferring genes into the germline, the expression of natural and hybrid genes and phenotypic changes that have occurred in transgenic mice are described by Palmiter and Brinster in *Ann. Rev. Genet.* 20 (1986) 465–499. Methods of foreign gene insertion, applications to foreign gene expression, and the use of transgenic mice to study immunological processes, neoplastic disease and other proliferative disorders are described by Gordon in *Intl. Rev. Cytol.* 115 (1989), 171–299.

The phenotypes of insertional mutations are often recessive and therefore only apparent when the transgenic mice are bred to homozygosity. The integrated DNA provides a molecular "handle" for the recovery and analysis of the mutated gene, as illustrated by the analysis of the embryonic lethal mutation resulting from the retroviral insertion of the Moloney murine leukemia virus into the 5' end of the alpha-1(I)-collagen gene, as described by Schnieke, et al, *Nature*, 304 (1983) 315–320.

Very few cases of insertional mutagenesis in transgenic mice have been reported to date and these include two mutations with limb deformities [See: Overbeck et al, *Science*, 231 (1986) 1574–1577; Woychik et al, *Nature*, 318 (1985) 36–40]; one with a defect in spermatogenesis [See: Palmitter et al, *Cell*, 36 (1984) 869–877]; and a number of developmental lethal mutations [See for example: Mahon et al, *Proc. Nat. Acad. Sci. U.S.A.*, 85 (1988) 1165–1168; and McNeish et al, *Science*, 241 (1988) 837–839].

The "rotating rodent" has been used for more than 15 years as a model in studies addressing the function of the dopaminergic nigrostriatal component of the basal ganglia component of the brain. Ungerstedt in *Acta Physiol. Scand.*, Suppl. 367 (1971) 49–66, demonstrated that high rates of circling behavior can be elicited by amphetamine, a dopamine releaser, or apomorphine, a dopamine agonist, in rats that had been unilaterally depleted of dopamine by 6-hydroxydopamine lesions. Furthermore, circling behavior has been investigated in humans [See: Bracha et al, *Brain Res.*, 411 (1987) 231–235], particularly in patients with hemi-parkinsonism [see: Bracha et al, *Life Sci.*, 40 (1987) 1127–1130] and schizophrenia [See: Bracha, *Biol. Psychiatry*, 22 (1987) 995–1003] and are understood to be mediated by components of the dopaminergic system.

Therefore, there exists a need for an animal which expresses a circling phenotype, without the other behavioral characteristics of the "shaker-waltzer" syndrome for us as a model in investigating the molecular genetic mechanisms that determine specific aspects of brain function and behavior. Additionally, this animal may be useful to evaluate new and potentially more effective agents for the therapeutic treatment of disorders involving dopaminergic dysfunction such as Parkinsonism and schizophrenia.

SUMMARY OF THE INVENTION

Accordingly, it is the primary object of the present invention to provide a transgenic non-human mammal as a result of introducing genetic material into the genome of the mammal, whereby the genetic material alters or disrupts an endogenous genetic locus affecting motor function.

Another object of the present invention is to provide such a transgenic mutant and, preferably a mouse which is a rodent.

The present invention provides a transgenic non-human mammal which exhibits a circling phenotype resulting from an insertional mutation. The insertional mutation is caused by introducing genetic material into the genome of the mammal, or an ancestor thereof, at an embryonic stage. The genetic material appears to alter or disrupt an endogenous genetic locus affecting motor function, resulting in the mutation.

The genetic material may comprise an exogenous DNA sequence and is introduced into the mammal by one of several methods which include microinjection of embryos at a pronuclear stage, retroviral infection of mouse embryo cells or embryonic stem cell-mediated gene transfer. The mammal is of the rodent family, and preferably a mouse.

In an embodiment of the present invention, fertilized eggs were microinjected with exogenous DNA containing a member of the renin structural gene family. Integration of the microinjected genetic material into the host genome may result in an insertional mutation. The phenotypes of insertional mutations are often recessive and, therefore, any noticeable trait caused by lack of gene function may only become apparent when the animal is bred to homozygosity. In addition, descendants of the transgenic animal that are homozygous for the particular gene will also display the phenotypic trait.

In a more particular embodiment of the present invention, transgenic mouse lines were made by microinjection of about a 24 kb XhoI genomic DNA fragment containing the mouse Ren-$2^d$ renin gene into $BCF_1$, (C57BL/10Ros$^{pd}$× C3H/HeRos) fertilized eggs. This fragment comprises approximately 5 kb of upstream, 10 kb of intron-exon and 9 kb of downstream Ren-$2^d$ sequences. One transgenic mouse line bred to homozygosity, designated TgX15 (also known as chakragati mice), was found to exhibit a circling phenotype. It is believed that the phenotype is specific for a particular integration site rather than the sequence or the expression of the transgene.

The circling phenotype appears to have disrupted an endogenous genetic locus affecting motor function. Furthermore, the circling behavior may represent an aberration associated with nigrostriatal neurons of the brain, and may affect one or more related pathways of neurotransmitters such as dopamine, adrenaline, noradrenaline, serotonin or GABA. The mice of the present invention which exhibited the circling phenotype i.e. TgX15 line, had significantly elevated dopamine receptor binding sites in the nigrostriata.

On the basis of this circling phenotype, and the ability to use the integrated DNA causing this trait in localizing the chromosome containing the insertion and the affected genetic coding information thereof, the transgenic mice of the present invention ("chakragati mice") may be an important resource for investigating the molecular genetic mechanisms that determine specific aspects of brain function and behavior.

Other objects, features and advantages of the present invention will become apparent from the following detailed description, taken in conjunction with the accompanying drawings.

DETAILED DESCRIPTION

The present invention provides a transgenic mouse line which exhibits a circling behavior phenotype occurring almost continually at night and in response to stress e.g., hand clapping, during the daytime as a result of insertional mutagenesis. This mutant was one of 19 transgenic mouse lines made by microinjection of a 24 kb XhoI genomic DNA fragment containing the mouse Ren-$2^d$ renin gene into BCF$_1$ fertilized eggs. This fragment contained 5 kb of upstream, 10 kb of intron-exon and 9 kb of downstream Ren-$2^d$ sequences. The genomic sequences flanking the insertional mutation map to, or corresponds to chromosome 16. Several of these lines were bred to homozygosity but only one, designated TgX15 or chakragati mice, exhibited the circling behavior.

Homozygous transgenic mice of the TgX15 mouse line expressed the circling phenotype while heterozygous transgenics appeared normal. The matings indicated that inheritance of the phenotype was consistent with an autosomal recessive mode at a single locus. It was also determined that dopamine D$_2$ receptor binding sites in the striata of the circling mice were significantly elevated by about 31% compared to normal heterozygous transgenic mice. Other transgenic lines constructed with the same transgene appear normal i.e., no circling phenotype, suggesting that in the TgX15 line, a genetic locus significant in mammalian motor behavior has been disrupted. That is, the transgene integration in the TgX15 mouse line has apparently disrupted an endogenous genetic locus affecting motor function. This is believed to be the first instance in which insertional mutagenesis has resulted in a well-characterized behavioral abnormality. Further neurochemical and neuroreceptor analysis of the mutant should help in the understanding of the molecular mechanisms of motor function.

EXAMPLE 1

DNA Construct

Strains of mice have been found to carry one or more renin structural genes which include at least three distinct genes: Ren-$1^c$, Ren-$1^d$, and Ren-$2^d$. Cosmid clone cosDBA-1, containing a copy of the Ren-$2^d$ gene, is described by Field et al. *Mol. Cell. Biol.*, 4 (1984) 2321–2331, which disclosure is hereby incorporated by reference. To construct transgenic mice, a 24 kb restriction fragment containing the Ren-$2^d$ was removed from cosmid clone cosDBA-1 by restriction enzyme treatment with XhoI and isolated on a 10–20% sucrose gradient in 10 mM Tris-Cl pH8.0, 10 mM EDTA, 200 mM sodium acetate. The fragment was further purified from gradient fractions by ethanol precipitation and CsCl gradient centrifugation. The DNA was adjusted to a concentration of 1 ug/ml in TE buffer, and stored at -20°C until used. In addition to containing the Ren-$2^d$ gene, the XhoI fragment also contains 5.3 kb located 5' of the major transcription start site, and 9.5 kb located 3' of the polyadenylation site.

EXAMPLE 2

Production of Transgenic Mice

Figure 1:
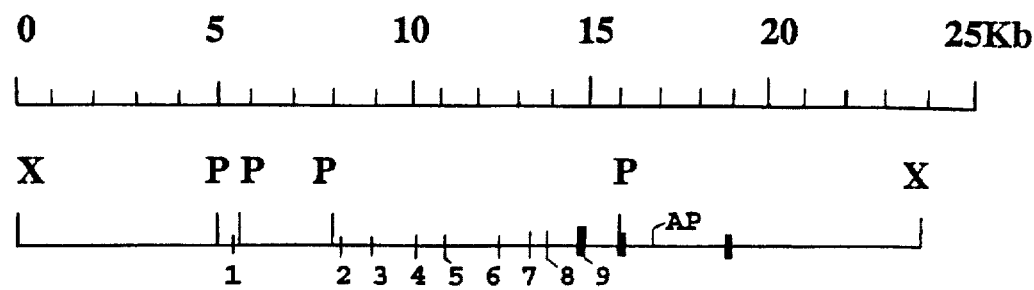
FIG. 1 shows a diagrammatic representation of the 24 kb XhoI restriction fragment, containing the Ren-$2^d$ gene and flanking sequences, isolated from cosmid clone cosDBA-1.

The XhoI fragment containing the mouse Ren-$2^d$ renin gene, as shown in FIG. 1, was microinjected into one-cell fertilized mouse eggs at pronuclear stage. The fertilized eggs BCF$_1$, derived from a cross of (C57BL/10Ros-$P^d$×C3H/HeRos) mice, were implanted into and fostered by Ha/1CR female mice. The mice, maintained on a 12 hour light-dark cycle, were obtained from West Seneca Laboratories, West Seneca, N.Y. Nineteen (19) transgenic mouse lines were made in accordance with this procedure. Several of these lines were bred to homozygosity, but only one of these, designated TgX15 or chakragati mice, exhibited a circling phenotype. This suggested that the phenotype was specific for a particular integration site rather than the sequence or the expression of the transgene. The overall frequency of insertional mutation in transgenic lines, including visible mutations and prenatal lethal mutations, has been estimated to be between 5% and 10% (Meisler, (1992), *Trends in Genetics* 8:341–345). This frequency is consistent with the observed frequency of the insertional mutation in the development of the mice of the present invention (1 out of 19 or 5.2%). This frequency is further supported by Wagner et al., U.S. Pat. No. 5,175,385, wherein 4 transgenic pMTIF-beta [A] mice were produced out of 140 animals produced, and 2 transgenic pMTIF-beta[B] mice were produced out of 40 animals produced.

EXAMPLE 3

Characterization of the Transgenic Mice

Figure 2:
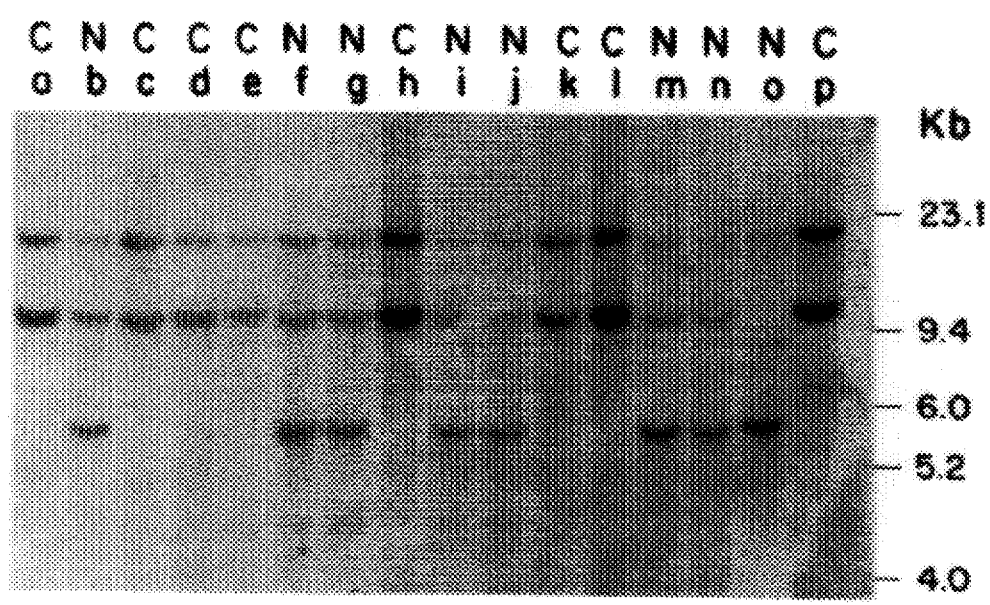
FIG. 2 shows a Southern blot analysis of restriction fragments from Bgl II-digested genomic DNA.

The transgenic mice were analyzed for expression of the transgene using the method of primer extension analysis described by Field and Gross, *Proc. Natl. Acad. Sci. USA*, 74 (1985) 5569–5573; the disclosure of which is hereby incorporated by reference. This method differentiates between the expression of the Ren-$2^d$ transgene from that of the endogenous Ren-$1^c$ gene. No evidence of transgene expression was found in the brains, livers, and submaxillary glands of mice that were heterozygous or homozygous for the transgene. A very minimal amount of expression was detected in the kidneys of mice homozygous for the transgene. The size of the insert (integrant), integrated into the genome of the mice, was about 65–70 kb comprising two and one half copies of the XhoI fragment containing the Ren-$2^d$ transgene. The integrant contained copies of the fragment in a head-to-tail tandem array. A DNA fragment from the host genome, flanking the 3' end of the integrant, was found to map to sequences on chromosome 16. Genomic DNA isolated from mice tail biopsies was treated with restriction enzyme Bgl II. The digest was analyzed for restriction fragment length polymorphisms (RFLPs) in Southern blot analysis to identify mice that were either homozygous or heterozygous for the integrant. With reference to FIG. 2, lanes a–n represent DNA samples from progeny of a heterozygous transgenic mated with a homozygous transgenic; lane o represents a DNA sample from a non-transgenic mouse of parental strain $BCF_1$; and lane p represents a DNA sample from a transgenic mouse of the present invention which exhibits the circling phenotype. Homozygous transgenic animals may be identified by the presence of a 10 kb restriction fragment and the absence of a 6 kb restriction fragment as exhibited by the DNA samples represented in FIG. 2, lanes a,c,d,e,h,k,l, and p. The homozygous transgenic animals exhibited the circling behavior as denoted by the "C" in FIG. 2. The DNA from non-transgenic animals have the 6 kb restriction fragment but lack the 10 kb fragment. The DNA from heterozygous transgenic animals have both the 10 kb and 6 kb restriction fragments. Neither the non-transgenic nor the heterozygous transgenic mice exhibit circling behavior as denoted by the "N" in FIG. 2. The 23 kb restriction fragment shown in FIG. 2 was due to a Bgl II restriction site further downstream of the integrant.

To determine if the circling phenotype cosegregated with the insertion site, heterozygous transgenic or homozygous transgenic mice were bred with each other or with parental strain $BCF_1$. The results of the matings suggested that inheritance of the phenotype was consistent with an autosomal recessive mode at a single locus. From the matings, the circling phenotype was observed as early as one to two weeks of age in the homozygous transgenic animals of the present invention. The line TgX15 was used as a pedigree to establish that the integrant was transmitted for more than thirty generations now, without any apparent genetic rearrangements in the integrant and the flanking sequences of the host genome.

The circling behavior was quantitated in a cylindrical rotometer. This apparatus discriminates between rotations and random movement and between rotations in different directions. The rotometer and method of use is described by Greenstein and Glick, *Pharmac. Biochem. Behav*, 3 (1975) 507–510, the disclosure of which is hereby incorporated by reference. The circling behavior was quantitated as (1) net turns, and (2)% preference as defined by the following formulae:

Net turns = (full turns in preferred direction) − (full turns in non-preferred direction)  (1)

$$\% \text{ Preference} = \frac{\text{(full turns in preferred direction)}}{\text{(total number of full turns)}} \times 100 \quad (2)$$

The % preference parameter enables comparisons between mice independent of the total activity. The quantitation of nocturnal circling behavior of the mice of the present invention, and of normal heterozygous litter-mates is shown in Table 1. Spontaneous nocturnal rotation by rodents has been reported to be a normal phenomenon. However, the mice of the present invention, when compared with the normal litter-mates, show a significant increase in net rotations and % preference in circling behavior.

TABLE 1

Quantitation of Circling Behavior

| | Normal litter-mates (n = 82) | Homozygous transgenic mutants (n = 70) |
|---|---|---|
| Net turns | 88.8 ± 11.0 | 729.5 ± 176.6* |
| Total turns | 140.0 ± 12.7 | 896.1 ± 198.2* |
| % Preference | 81.3 ± 1.6 | 84.5 ± 1.9 | n = number in study
*p < 0.001

Circling behavior has been induced by chemicals in rats having lesions which deplete levels of dopamine. Circling behavior exhibited in humans is also thought to be mediated by components of the dopaminergic system. Since circling behavior has been associated with an imbalance of nigrostriatal function, the levels of the neurotransmitters dopamine, serotonin, and norepinephrine, and their metabolites which include dihydroxyphenylacetic acid, homovanillic acid and 5-hydroxyindoleacetic acid, were measured in the striatia of mice of the present invention and heterozygous mice by high pressure liquid chromatography. Similar measurements were also made in the nucleus accumbens and cortex structures which are known to modulate striatal mechanisms involved in circling. The results of the analysis (data not shown) suggest that there is no significant difference between mice of the present invention, and normal heterozygous mice, in the levels of neurotransmitters and metabolites.

Radioligand binding assays were performed to analyze the density of dopamine $D_2$ receptor binding sites in the striatum of mice of the present invention and normal heterozygous mice. The binding analysis was performed essentially as described by Lyon et al., *J. Neuroscience* 6 (1986) 2941–2948, which disclosure is hereby incorporated by reference. The density of dopamine $D_2$ binding sites are assayed by the ability of the striata to maximally bind $^3$H-N-methylspiperone ($B_{max}$). Dissociation constants ($K_D$) between the ligand and receptor were also measured. The data, represented in Table 2, showed that there was a significant increase in the ability of the striata from mice of the present invention to bind to the radioligand when compared to normal heterozygous mice. Also, there appears to be no difference in the ability of either group of mice in the dissociation constants of the ligand with the receptor. These results suggest that an up-regulation of dopamine $D_2$ receptors may be associated with the circling behavior of the mice of the present invention.

TABLE 2

| | Homozygous transgenic mice | Heterozygous litter-mates |
|---|---|---|
| $B_{max}$ (fmol/mg protein) | 120.5 ± 8.8* | 91.7 ± 9.3 |
| $K_D$ (nM) | 0.081 ± 0.013 | 0.073 ± 0.008 |

*p < 0.05, results presented as mean ± s.e.m.

Dopamine $D_2$ autoradiography was conducted on slide-mounted brain tissue sections of the transgenic mice of the present invention (chakragati mice), and normal mice of the same species ("normal mice"), using the protocol of Burke et al. (1988, *Life Sci.* 42:2097–2014) with some minor modifications. The chakragati mice showed bilateral elevations in dopamine $D_2$ densities in each subregion of the striatum as compared to normal mice (mean $D_2$ receptor elevation approximately 30%). The chakragati mice also showed a much larger hemispheric asymmetry in $D_2$ receptor densities, resulting in an enhanced medial-to-lateral $D_2$ gradient on one side of the brain. Analysis of the $D_2$ receptor elevations with respect to the preferred direction of spontaneous nocturnal rotation revealed that in chakragati mice, $D_2$ receptors in both lateral regions contralateral to the preferred direction of rotation were significantly greater than those on the ipsilateral side.

Dopamine $D_1$ autoradiography performed on tissue sections of chakragati mice and normal mice using the protocol of Savasta et al. (1986, *Brain Res.* 375:291–301) with some minor modifications. Striatal dopamine $D_1$ receptor densities in the chakragati mice were neither elevated nor differentially asymmetric as compared with normal mice. This suggests that unlike $D_2$ receptors, abnormal $D_1$ receptor function does not underlie the circling phenotype in chakragati mice.

There are a number of spontaneous mouse mutants that express the "shaker-waltzer" syndrome, which is characterized by a tendence to run in circles, hyperactivity, jerking head movements and abnormal responses to change in position. All of these mutants have gross deformities and degeneration of the bony membranous labyrinths of the inner ear. In contrast, physiological and behavioral analyses of the transgenic mice of the present invention, exhibiting the circling phenotype, show no evidence of inner ear deformities, degeneration, hearing loss, hyperactivity or jerky head movements. Thus, it would appear that in the mice of the present invention, a central, rather than vestibular, derangement caused the circling phenotype.

EXAMPLE 4

Model for Disease

The transgenic mice of the present invention can be used to evaluate new and potentially more effective agents for therapeutic treatment of disorders involving dopaminergic dysfunction, and particularly involving $D_2$ receptors in the nigrostriata, such as in Parkinsonism and schizophrenia. Chakragati mice can be used to screen for preclinical antipsychotic potency of recently developed antipsychotic agents, and new dopaminergic agents having similar chemical structures.

Embodiment A—Antipsychotic Agents

Chakragati mice represent a novel and unique animal model with which to test "antipsychotic" potency since they have a reproducible and persistent overactivity in their central dopamine systems caused by a selective increase in striatal $D_2$ receptor subtypes. Current animal models used to test antipsychotic potency rely on testing the ability of novel compounds to block behaviors elicited by an acute and transient activation of central dopamine function.

One existing model that produces longer-lasting, unilateral hyperactivity in central dopamine function is the 6-OHDA-lesioned rodent. The chakragati mice model, while having all the features of this model, also has a distinct advantage over the 6-OHDA model. The chakragati mice model is uniquely appropriate for testing the antipsychotic potency of new dopamine autoreceptor agonists as the drugs require an intact, and possibly overactive, presynaptic dopamine pathway to work. In the 6-OHDA model only excessive dopamine function occurring postsynaptically can be mitigated since the presynaptic input is unilaterally destroyed.

Antipsychotic agents reduce dopamine over-activity by mechanisms including 1) stimulating dopamine autoreceptors on dopamine neurons, thereby reducing the functional activity of the dopamine system; and 2) blocking postsynaptic dopamine receptors on dopaminoreceptive neurons or other neurotransmitters systems that are secondary to the dopaminoreceptive neurons. Antipsychotic agents, which may be evaluated for antipsychotic potency in the chakragati mice, include atypical drugs, partial agonists, and autoreceptor agonists.

Atypical drugs include risperidone, remoxipride, novel cyclic benzamides, amperozide, and novel compounds that are structurally similar to these drugs. These drugs, which block postsynaptic dopamine receptors and other neurotransmitter receptors, have shown clinical efficacy. Partial agonists include partial ergolines and aminoergolines, and related aminothiazole, aminooxazole, and pyridine and benzenoid analogues. These drugs stimulate postsynaptic dopamine receptors on dopaminoreceptive cells in a manner that is less efficient (and therefore "partial") than endogenous dopamine. The functional net effect of this would be a decrease in postsynaptic dopamine activity. Typically, these drugs have high or "preferential" affinity for $D_2$ receptors. In contrast, full dopamine agonists, including quinpirole and quinelorane, would be expected to stimulate the dopamine receptive cells in a very efficient manner. Such stimulation would be expected to increase the circling behavior of the chakragati mice. Autoreceptor agonists, including roxindole, reduce overall dopamine activity by stimulating autoreceptors found on dopamine neurons. Such stimulation, unlike dopamine's actions at postsynaptic sites, reduce the activity of the dopaminergic pathways.

The antipsychotic agents can be evaluated for antipsychotic potency by introducing the agent into the chakragati mice by a suitable route of administration (depending on the chemistry of the agent) in various doses, and noting the drugs effects, if any, on the circling phenotype and locomotor hyperactivity. Low dose ranges may approach the pg/kg to ng/kg range depending on the agent. High dose ranges may be >10–20 mg/kg depending on the agent. Various dose ranges need to be evaluated as an increase in the circling response may be seen at a low and/or moderate dose range; but behavioral disruption may occur, with excessive stimulation of dopamine receptors, at extremely high dose ranges.

Embodiment B

Quinpirole has been used as a reference standard for pharmacological studies of dopamine receptors. Transgenic mice of the present invention were treated with the selective dopamine $D_2$ agonist quinpirole, and then assayed for their rotational and stereotypic responses to the pharmacologically active agent. In this experiment, the transgenic mice received several doses of quinpirole over a period of a few weeks with 5 days separating successive dosing periods. Since behavioral sensitization to quinpirole, when present, can depend on the order of multiple dosing, care was taken to ensure that the dosing schedule did not vary systematically between the mouse groups. In this study, two age groups of transgenic and normal mice were used: a younger age group consisting of young adult mice of 60–90 postnatal days (PND 60–90); and an older age group consisting of mice of 180–210 postnatal days (PND 180–210).

After a 15 minute habituation period, baseline rotation of each mouse was recorded for 1 hour. Baseline or preinjection levels of stereotypy were considered to be non-existent and were therefore not measured. Immediately after recording the baseline rotation, transgenic mice and control mice were injected subcutaneously with 0.0, 0.25, 1.0, or 2.5 mg/kg of quinpirole HCl in normal saline and rotation and stereotypic behavior was assessed for 1 hour. Left and right rotations were separately totalled over the 1 hour period for each mouse and a net rotational difference was determined.

Net rotations equalled rotations in the preferred direction minus those in the nonpreferred direction. Examination of quinpirole-induced rotation revealed that normal control mice at either of the age groups used (PND 60–90 and PND 180–210) show no significant change in baseline net turns after injection with saline, or any dose of quinpirole (See Table 3). In contrast, the transgenic mice at PND 60–90 showed a dose-related increase in net turns over baseline levels at the 1.0, and 2.5 mg/kg doses but not at the 0.25 mg/kg dose. Injection per se did not account for the increases since these transgenic mice actually showed a significant decrease in net turns after the saline injection. In contrast, older transgenic adult mice (at PND 180–210) displayed dose-related decreases in net turns after the 1.0 and 2.5 mg/kg doses, but no change after the saline or 0.25 mg/kg injections (See Table 3).

The circling phenotype of the transgenic mice of the present invention is thought to be caused by the elevated and asymmetric $D_2$ receptor density present in these mice. Additional support for a role of asymmetric $D_2$ receptors in the transgenic mice in the circling phenotype is illustrated by the quinpirole studies. Young adult transgenic mice (PND 60–90), having a significantly higher and asymmetric $D_2$ receptor density than normal mice, rotate to the side opposite to that with the greater number of $D_2$ receptors ("contralaterally"). Treatment of these mice with a full dopamine agonist (quinpirole) stimulates turning contralateral, resulting in increased rotation.

Two age groups of control mice and the transgenic mice of the present invention were included in the embodiment of evaluating the effect of quinpirole on circling behavior. It is known in the art that age-related changes occur to dopamine receptors in the region of the brain comprising the nigrostriata. More specifically, there is an age-related decline in the density of dopamine receptors in striata from mammals such as mouse species and humans (Severson et al. 1985, *J. Pharmacol. Exp. Ther.* 233:361–367). A decrease in $D_2$ asymmetry observed in the lateral striatal regions of the older group (PND 180–210), as compared to the younger group (PND 60–90), of chakragati mice may be one of a number of factors responsible for the age-related differences in dopamine agonist-induced behaviors.

Since the young adult transgenic mice (PND 60–90) consistently and reproducibly show an expected phenotypic response upon treatment with a dopamine agonist (quinpirole at a concentration in dosage in the range of 1–2.5 mg/kg), this age group of young adult mice may preferentially be used in evaluating the potency of antipsychotic agents preclinically.

Figure 3:
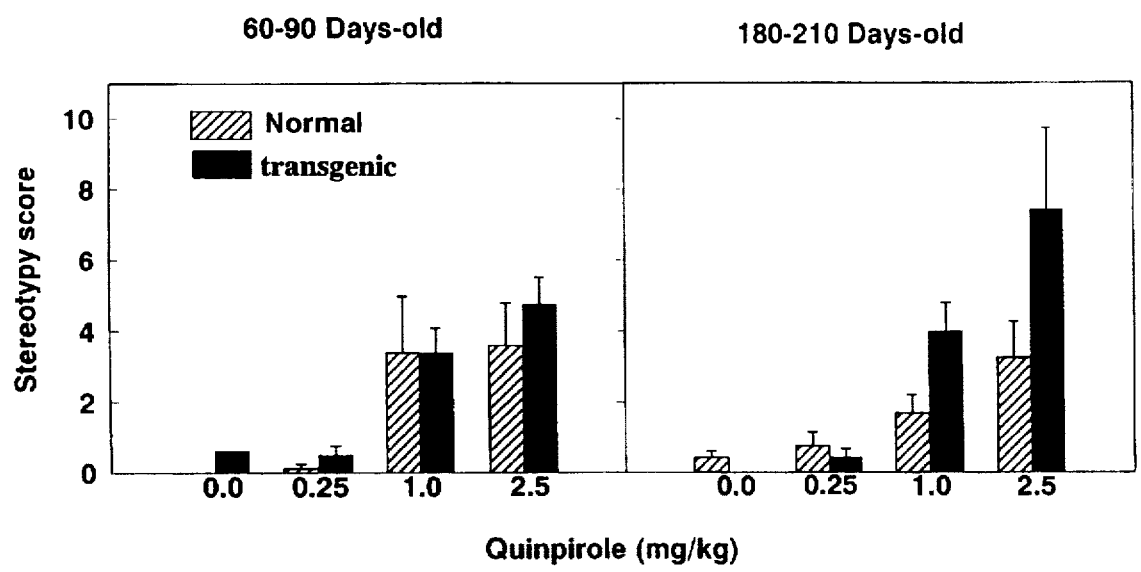
FIG. 3 shows mean (±S.E.M.) stereotypic sniffing responses of the transgenic mice and normal mice from 2 age groups following treatment with different doses of a pharmacological agent, quinpirole.

Stereotyped sniffing behavior was the focus of stereotypy measurements. The selective stimulation of $D_2$ receptors by quinpirole without concomitant $D_1$ stimulation generally produces sniffing, the severity of sniffing being assessed using a rating scale in which mice were scored every 5 minutes for an hour. The stereotypy scoring is as follows: "0" indicates that sniffing was absent; "1" indicates intermittent sniffing; and "2" represents continuous or persistent sniffing. Individual scores were summed over the 1 hour test period with a possible maximum score being 24. Younger (PND 60–90) transgenic and normal control mice showed equivalent dose-related increases in stereotyped sniffing, whereas older transgenic mice (PND 180–210) showed greater sniffing than control mice at the 1.0 mg/kg dose only (FIG. 3).

Another possible explanation for the age-related differences in rotation (i.e., decreased in the (PND 180–210) group) is that the significantly increased stereotyping (sniffing behavior) seen in the older age group of chakragati mice may have competed with the expression of increased circling.

Embodiment C

The transgenic mice of the present invention provide a functionally different model in which to evaluate antipsychotic agents preclinically, then do rats with unilateral 6-hydroxydopamine lesions of the medial forebrain bundle ("6-OHDA-lesioned rodent"). Protein, morphometric, and histological data fail to indicate any gross observable alteration of cell populations intrinsic to the striata of chakragati mice. Further, the chakragati mice has both asymmetric and symmetric elevations in $D_2$ receptors (depending on the subregion of the striatum), normal bilateral nigrostriatal innervation and normal dopamine levels. In contrast, the 6-OHDA-lesioned rodents contain unilateral denervation, asymmetric elevation in $D_2$ and possibly $D_1$ receptors from a compensatory reaction to presynaptic denervation, asymmetric nigrostriatal dopamine function, and depletion of dopamine levels. Further, 6-OHDA-lesioned rodent testing involves the elicitation of circling with a dopamine agonist, followed by testing the ability of a putative antipsychotic drug in blocking the agonist-induced behavior.

The 6-OHDA-lesioned rodents have been shown to turn circles not only in response to $D_2$ agonists, but also in response to $D_1$ and mixed $D_1/D_2$ agonists. In contrast, the chakragati mice show a selective increase in striatal $D_2$ receptor subtypes versus $D_1$ receptors. Thus, the chakragati mice may be used to differentiate between an antipsychotic agent having $D_2$ antagonist activity versus an antipsychotic agent having $D_1$ antagonist activity or mixed $D_1/D_2$ antago-

TABLE 3

Net rotations in mice before and after quinpirole

| Age | Group | | Saline | Dose of qinpirole (mg/kg)** | | |
|---|---|---|---|---|---|---|
| | | | | 0.25 | 1.0 | 2.5 |
| PND 60–90 | Normal | (B) | 28.0 (8.0) | 17.7 (7.2) | 18.9 (6.0) | 18.3 (5.6) |
| | | (P) | 11.5 (4.0) | 5.5 (2.2) | 4.6 (2.0) | 9.4 (5.4) |
| | Transgenic | (B) | 94.8 (69.3) | 48.0 (27.8) | 76.1 (65.8) | 31.8 (20.5) |
| | | (P) | 32.6 (11.6)* | 26.1 (14.5) | 144.8 (73.6)* | 103.8 (58.8)* |
| PND 180–210 | Normal | (B) | 23.4 (6.6) | 20.4 (5.5) | 26.0 (5.0) | 24.0 (6.0) |
| | | (P) | 18.9 (5.0) | 3.5 (1.1) | 7.5 (3.3) | 7.6 (3.5) |
| | Transgenic | (B) | 44.1 (20.0) | 19.9 (5.4) | 74.6 (45.9) | 70.9 (46.6) |
| | | (P) | 29.4 (13.2) | 3.8 (1.9) | 11.9 (5.5)* | 16.9 (8.4)* |

*Significant difference (LSD tests) between baseline (B) and postinjection (P) scores, $P < 0.05$.
**Values represent mean ± (S.E.M.).

nist. For example, treatment of 6-OHDA-lesioned rodents with apomorphine (a prototypic mixed $D_1/D_2$ agonist) elicits robust circling behavior. In contrast, the effect of a apomorphine treatment on chakragati mice has been shown to not significantly differ compared to the normal control mice. The chakragati mouse may be a more appropriate model since abnormal dopamine $D_1$ receptor function is not observed post-mortem in schizophrenic patients. Moreover, current $D_1$ antagonists tested in clinical trials have not been therapeutically beneficial.

Further, the animals of the present invention may be used as a resource for investigating the molecular genetic mechanisms that determine specific aspects of brain function and behavior. In particular, the insertion site of the genome of the transgenic animals, and surrounding genomic sequences, may be studied by using the insertional DNA as a probe to isolate these genomic sequences and further define their role in motor function and behavior. Heterozygous Tgx15 mouse embryos have been deposited on Jun. 4, 1997 with the American Type Tissue Culture Association (ATCC, Rockville, Md.) under Designation No. 72032.

Changes, modifications, and other embodiments, apparent to one of ordinary skill in the art from the foregoing description, are intended to be included within the spirit of this application and within the scope of the appended claims.

We claim:

1. A transgenic mouse, from a mouse line designated TgX15, exhibiting a circling behavior phenotype as a result of an insertional mutation caused by introducing a Ren-$2^d$ transgene into chromosome 16 of said mouse, or an ancestor thereof, at an embryonic stage such that said transgene disrupts an endogenous function, resulting in said mutation, wherein the transgenic mouse demonstrates an increase in dopamine binding receptors in the nigrostriata when compared to mice of the same species which do not contain the insertional mutation.

2. The mouse of claim 1, wherein said transgene disrupts an endogenous genetic locus affecting motor function.

3. The mouse of claim 1, wherein inheritance of said circling phenotype is consistent with an autosomal recessive mode at a single locus.

4. The mouse of claim 1, wherein said mouse has no deformities or degeneration in the bony and membranous labyrinths of the inner ear.

5. The mouse of claim 1, wherein said circling phenotype occurs almost continuously at night, and in response to stress in the daytime.

6. A method of testing the therapeutic activity of a pharmacological agent on dopaminergic disorders of the nigrostriata region of the brain comprising administering an effective amount of said pharmacological agent to the mouse of claim 1, and evaluating said agent's effect on the circling phenotype of said mouse.

* * * * *